US00PP30281P2

(12) United States Plant Patent
Hansen

(10) Patent No.: US PP30,281 P2
(45) Date of Patent: Mar. 5, 2019

(54) ***AGAVE* PLANT NAMED 'RIPPLE EFFECT'**

(50) Latin Name: *Agave*
Varietal Denomination: Ripple Effect

(71) Applicant: Hans A Hansen, Zeeland, MI (US)

(72) Inventor: Hans A Hansen, Zeeland, MI (US)

( * ) Notice: Subject to any disclaimer, the term of this patent is extended or adjusted under 35 U.S.C. 154(b) by 0 days.

(21) Appl. No.: 15/932,169

(22) Filed: Feb. 14, 2018

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique *Agave* plant named 'Ripple Effect' characterized by outright to horizontal plant habit of broadly-lanceolate, slightly-cupped, variegated leaves having wide yellowish-cream margins and contrasting bluish-green centers. The leaves have large colorful marginal and apical spines. The plant is useful in the landscape as a specimen, en masse, or also in a container in the home or landscape.

1 Drawing Sheet

Botanical classification: *Agave*.
Variety denomination: 'Ripple Effect'.

BACKGROUND OF THE INVENTION

The present invention relates to the new and distinct *Agave* plant, *Agave* 'Ripple Effect' selected by the inventor at a perennial nursery in Raleigh, N.C., USA as an uninduced whole-plant mutation from a tissue cultured crop of *Agave* 'Mr. Ripple' (not patented) in the summer of 2011. The new plant has been successfully asexually propagated by tissue culture at a nursery in Zeeland, Mich. Shoot tip tissue culture propagation systems have been found produce stable and identical plants that maintain the unique characteristics of the original plant.

No plants of *Agave* 'Ripple Effect' have been sold, in this country or anywhere in the world, prior to the filing of this application, nor has any disclosure of the new plant been made prior to the filing of this application with the except that which was disclosed within one year of the filing of this application and was either derived directly or indirectly from the inventor.

BRIEF SUMMARY OF THE INVENTION

*Agave* 'Ripple Effect' is a sport of 'Mr. Ripple'. 'Mr. Ripple' was discovered east of Ciudad del Maiz in San Luis Potosi, Mexico in 2001 and is suspected of being either from the species *A. salmaina* or a hybrid between *A. salmiana* and *A. protomamericana*. 'Ripple Effect' differs from its parent, 'Mr. Ripple', as well as all other *Agaves* known to the applicant. The most similar known *Agave* cultivars other than the parent are: *Agave americana* 'Marshmallow Cream' (not patented), *Agave americana* 'Opal' (not patented). 'Marshmallow Cream' has much narrower foliage and the leaf margins are more creamy white and the center more bluish-green. 'Opal' has narrower leaves with a narrower variegation and the leaf center is more blue-green. Compared with *Agave americana* 'Aureo-marginata' (not patented) the new plant has shorter broader leaves with a broader variegation. *Agave salmiana* 'Butterfinger' (not patented) has more upright habit, narrower leaves and the center of the leaves is darker green.

Compared with 'Mr. Ripple' the new plant has a broad yellowish cream margin.

*Agave* 'Ripple Effect' differs from all other *Agaves* known to the applicant, by the combination of the following traits:

1. Foliage with large, colorful, marginal spines protruding from broad variegated leaves and leaving an imprint on the adaxial and abaxial surfaces of other leaves;
2. Leaves have wide yellowish-cream margins and contrasting bluish-green leaf centers;
3. Leaves have slightly cupped shape;
4. Habit is mounded with mostly outright to horizontal foliage.

BRIEF DESCRIPTION OF THE DRAWINGS

The photograph of the new plant demonstrates the overall appearance of the new plant including the unique traits as a five-year old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
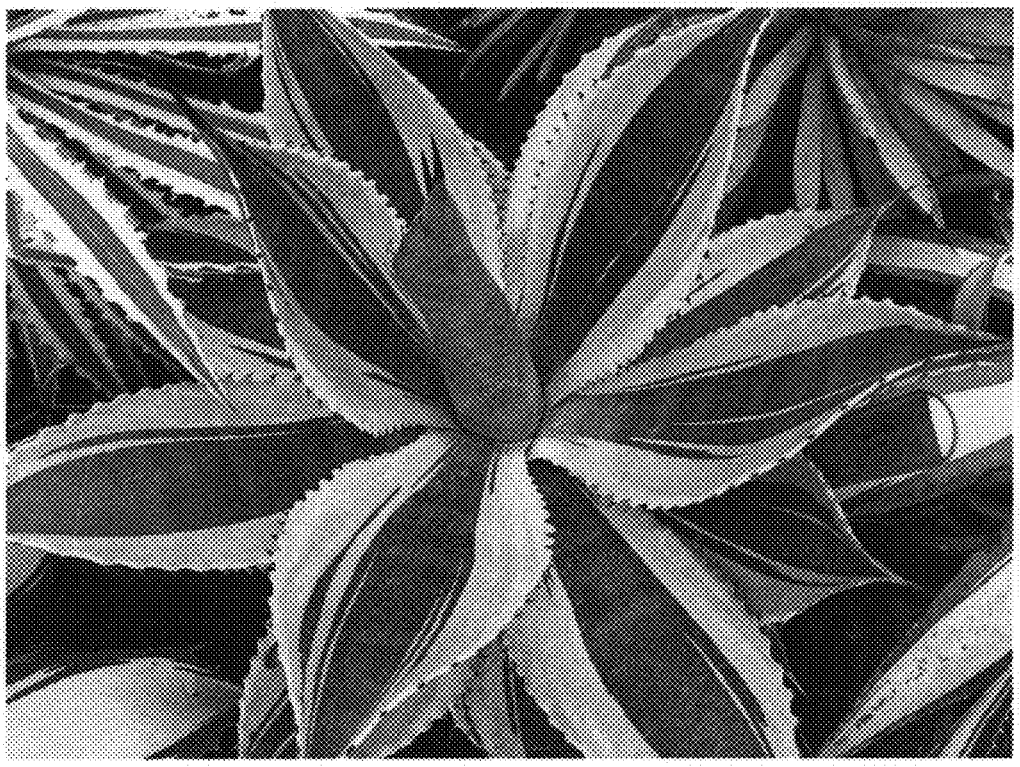
FIG. 1 shows the habit of the foliage of the whole plant.
Figure 2:
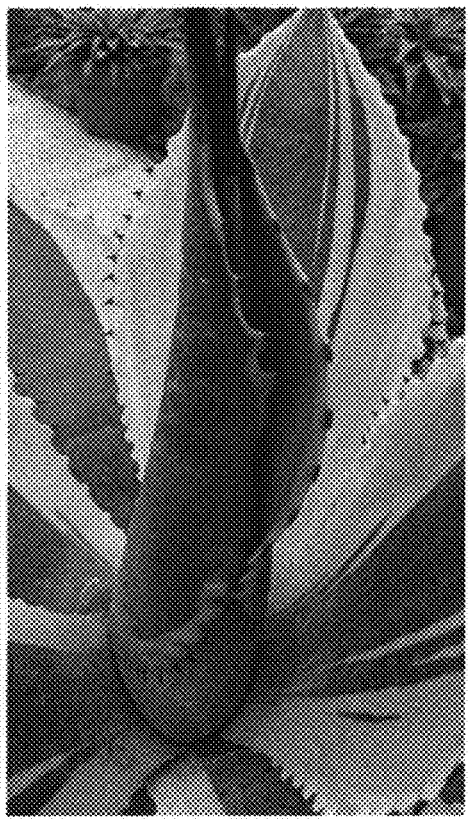
FIG. 2 shows a close-up of the new plant in a container with new unfurling foliage in the center displaying imprinting from marginal spines of other leaves.

The following descriptions and color references are based on the 2015 edition of The Royal Horticultural Society Colour Chart except where common dictionary terms are used. The new plant, *Agave* 'Ripple Effect', has not been observed under all possible environments. The phenotype may vary slightly with different environmental conditions, such as temperature, light, fertility, moisture and maturity levels, but without any change in the genotype. The following observations and size descriptions are of a three-year old plant in a commercial wholesale greenhouse in Zeeland, Mich. with supplemental water and fertilizer as needed.

Botanical classification: *Agave;*

Variety denomination: 'Ripple Effect';

Sport parentage: Uninduced whole-plant sport of *Agave* 'Mr. Ripple';

Propagation: Garden division and sterile plant tissue culture;

Time to initiate roots from tissue culture: About 21 days;

Growth rate: Moderate to slow;

Crop time: About 20 weeks to finish during the summer in a 3.8 liter container from an established 2.5 cm tissue culture plug;

Rooting habit: Fleshy, lightly branching, with roots up to 20 cm long;

Root color: Nearest RHS 158C;

Plant shape and habit: Herbaceous tender perennial with basal rosettes of slightly cupped, broad, variegated, whorled leaves emerging from central base, producing a symmetrical outright to horizontal mound;

Plant size: Foliage height about 44.0 cm tall from soil line to the top of the leaves and about 62.0 cm wide at the widest point about just above soil line;

Foliage description: Broadly lanceolate, simple, fleshy; narrowly acute apex ending in long stiff spine; truncate sessile base; margin with sharp stiff spines pointing slightly outward in distal portion and backward in proximal portion; slightly cupped with outer leaf edges curled upward; glabrous and slightly glaucous abaxial and adaxial; attitude outwardly to slightly upward;

Number of leaves: About 44 per plant;

Leaf size: To about 35.0 cm long, 17.0 cm wide near middle and 22.0 mm thick near base; average 33.5 cm long, 15.5 cm wide near middle and 20.0 thick near base;

Leaf variegation dimensions: Adaxial margin to 21.0 mm wide in longitudinal middle and tapering to about 2.0 mm near apex; abaxial margin to about 55.0 mm in longitudinal middle and tapering to about 2.0 mm at apex; intermediate zone between yellowish-cream margins and bluish-green center widest in longitudinal center and not noticeable at abaxial surface or adaxial base or apex, to about 19.0 mm wide in adaxial longitudinal center; adaxial bluish-green center about 7.5 cm wide; abaxial bluish-green center about 12.0 cm wide; with frequent longitudinal stripes of bluish-green extending various random lengths into the intermediate zone;

Foliage fragrance: None observed;

Stem: To about 6.0 cm wide and about 4.0 cm tall; covered with leaves;

Leaf blade color:

*Mature adaxial*.—Margin blend between RHS 160A and RHS 11A, center nearest blend between RHS 137A and RHS NN177A, intermediate zone blend between RHS 138B and RHS 11A.

*Mature abaxial*.—Margin nearest blend between RHS 160A and RHS 11A, center nearest RHS NN137A.

*Expanding young adaxial*.—Margin nearest RHS 144B, center nearest RHS 144A and intermediate zone between RHS 144B and RHS N144B.

*Expanding young abaxial*.—Margin nearest RHS 144B, center nearest RHS 139A and intermediate zone nearest RHS 144A.

Spine: Apical spine to about 35.0 mm long; stiff and sharp; color base nearest RHS 166A, middle and apex nearest RHS 183A;

Marginal spines: Sharply pointed; stiff; pointing slightly outward in distal portion and backward in proximal portion; about 5.0 mm long and about 12.0 mm apart; color nearest RHS 5D;

Petiole: Sessile;

Veins: Absent;

Flower description: Flowers have not yet been observed;

Fruit and seed: Have not yet been observed;

Disease resistance: *Agave* 'Ripple Effect' has not been observed to be resistant to diseases common to *Agaves* beyond that which is normal for *Agave*. The plant is xeromorphic and survives well with minimal water once established. Hardiness at least from USDA zone 9 to 10. Full extent of winter hardiness has not been tested.

I claim:

1. A new and distinct cultivar of ornamental *Agave* plant named 'Ripple Effect' as herein described and illustrated.

* * * * *